United States Patent [19]
Steinmann et al.

[11] Patent Number: 5,962,683
[45] Date of Patent: Oct. 5, 1999

[54] OXAZOLINE COMPOUNDS AS STABILIZERS

[75] Inventors: Alfred Steinmann, Praroman, Switzerland; Rolf Mülhaupt, Freiburg, Germany

[73] Assignee: Ciba Specialty Chemicals Corp., Tarrytown, N.Y.

[21] Appl. No.: 08/877,449

[22] Filed: Jun. 17, 1997

[30] Foreign Application Priority Data

Jun. 28, 1996 [CH] Switzerland ............ 1631/96

[51] Int. Cl.$^6$ ............ C07D 263/14; C07D 413/10; C07D 413/14; C08K 5/353
[52] U.S. Cl. ............ 544/180; 544/215; 544/216; 544/219; 544/220; 544/221; 544/222; 544/223; 546/187; 546/199; 546/207; 546/209; 546/229; 546/246; 548/215; 548/216; 548/218; 548/225; 548/226; 548/227; 548/228; 548/229; 548/230; 548/231; 548/232; 548/233; 524/87; 524/91; 524/92; 524/93; 524/95; 524/100; 524/102; 524/103; 524/104; 549/551; 549/552
[58] Field of Search .................. 548/215, 216, 548/218, 225–233; 544/180, 215, 216, 219–223; 546/187, 199, 207, 209, 229, 246; 524/87, 91, 92, 93, 95, 100, 102, 103, 104; 549/551, 552

[56] References Cited

U.S. PATENT DOCUMENTS

| | | | |
|---|---|---|---|
| 4,843,087 | 6/1989 | Diana ............ | 514/374 |
| 5,039,746 | 8/1991 | Neugebauer et al. ........... | 525/152 |
| 5,039,781 | 8/1991 | Neugebauer et al. ........... | 528/216 |

FOREIGN PATENT DOCUMENTS

| | | |
|---|---|---|
| 0008507 | 3/1980 | European Pat. Off. . |
| 2031891 | 4/1980 | United Kingdom . |

OTHER PUBLICATIONS

Chem. Abst. 101:151798w.
Chem. Abst. 70:58976j.
Kelarev et al, Synthesis & Properties of Azoles & Their Derivatives, pp. 721–723.
Inata et al., Journal of Applied Polymer Science, vol. 33 3069–3079 (1987).
Birnbrich et al., Kunststoffe, 83, (1993) 11.

*Primary Examiner*—Frederick Krass
*Attorney, Agent, or Firm*—Luther A. R. Hall

[57] ABSTRACT

A description is given of compounds of the formula I

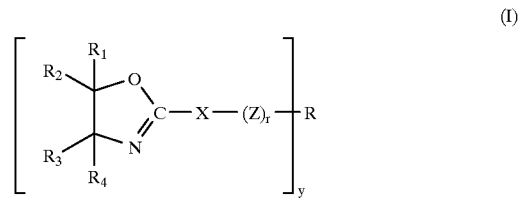

(I)

where r is 0 or 1 and y is a number from the range 1–3;

X is a direct bond or $-NR_8-$, $-CO-$, $-CONH-$ or $-COO-$ or a divalent aliphatic or mixed aromatic-aliphatic $C_1-C_{18}$ hydrocarbon radical;

Z is an aromatic, aliphatic or mixed aromatic-aliphatic $C_3-C_{18}$ hydrocarbon radical which is interrupted in the aliphatic moiety by one or more divalent functional groups, in each case in a carbon-carbon single bond, and/or in the aromatic or aliphatic moiety by one or more divalent functional groups, in each case in a carbon-hydrogen bond, possible functional groups being $-O-$, $-NR_8-$, $-S-$, $-SO-$, $-SO_2-$, $-CONH-$, $-CO-$ or $-COO-$;

R is a mono-, di- or trivalent radical of a sterically hindered amine or of a UV absorber from the class of the 2-hydroxyphenylbenzotriazoles, 2-hydroxyphenylbenzophenones, oxalanilides or 2-hydroxyphenyl-4,6-diaryltriazines or a di- or trivalent radical of a sterically hindered phenol;

$R_1$ and $R_2$, independently of one another, are H or $C_1-C_{12}$alkyl;

$R_3$ and $R_4$, independently of one another, are H, $C_1-C_{18}$alkyl or $-X-(Z)_r-R_5$;

$R_5$ is a monovalent radical of a sterically hindered amine or of a UV absorber from the class of the 2-hydroxyphenylbenzotriazoles, 2-hydroxyphenylbenzophenones, oxalanilides or 2-hydroxyphenyl-4,6-diaryltriazines or a radical of a sterically hindered phenol; and $R_8$ is H, $C_1-C_{18}$alkyl, $C_7-C_{11}$phenylalkyl, $C_2-C_6$alkoxyalkyl or $C_5-C_{12}$cycloalkyl. Compounds of the formula I can be employed with advantage for stabilizing organic material against the damaging effect of light, oxygen and/or heat.

10 Claims, No Drawings

OXAZOLINE COMPOUNDS AS STABILIZERS

The invention relates to new compounds of the oxazoline (4,5-dihydrooxazole) type which carry in position 2 a substituent which is effective as stabilizer, to polymers modified by reaction with these compounds, to organic material stabilized by addition of these compounds and to the corresponding use of the new compounds.

The use of compounds of the 2-oxazoline type as polymer additives for chain extension and for preventing phase separation phenomena in polymer alloys has been described, inter alia, by H. Inata and S. Matsumura, J. Appl. Polym. Sc. 33, 3069 (1987) and P. Birnbrich et al., Kunststoffe 83, 885 (1993).

Individual polyphenylene ethers with 2-oxazoline end groups are specified in U.S. Pat. No. 5,039,746.

The preparation of some 2-(hydroxyphenyl)oxazolines is described in U.S. Pat. No. 4,843,087, U.S. Pat. No. 5,039,781 and EP-A-8507, and by V. I. Kelarev et al., Khim. Geterotsiklicheskikh Soedinenii, 889 (1984), the two latter publications recommending the use of the products obtained as antioxidants.

It has now been found that hindered amines and UV absorbers which comprise one or more oxazoline groups, and hindered phenols which comprise 2 or more oxazoline groups, are also outstandingly suitable as stabilizers for organic material and for reactive coupling thereon.

The invention therefore provides first of all a compound of the formula I

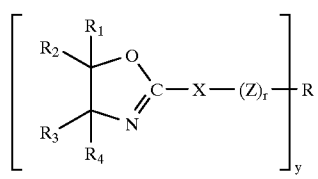

(I)

where r is 0 or 1 and y is a number from the range 1–3;

X is a direct bond or —$NR_8$—, —CO—, —CONH— or —COO— or a divalent aliphatic or mixed aromatic-aliphatic $C_1$–$C_{18}$ hydrocarbon radical;

Z is an aromatic, aliphatic or mixed aromatic-aliphatic $C_3$–$C_{18}$ hydrocarbon radical which is interrupted in the aliphatic moiety by one or more divalent functional groups, in each case in a carbon-carbon single bond, and/or in the aromatic or aliphatic moiety by one or more divalent functional groups, in each case in a carbon-hydrogen bond, possible functional groups being —O—, —$NR_8$—, —S—, —SO—, —$SO_2$—, —CONH—, —CO— or —COO—;

R is a mono-, di- or trivalent radical of a sterically hindered amine or of a UV absorber from the class of the 2-hydroxyphenylbenzotriazoles, 2-hydroxyphenylbenzophenones, oxalanilides or 2-hydroxyphenyl-4,6-diaryltriazines or a di- or trivalent radical of a sterically hindered phenol;

$R_1$ and $R_2$, independently of one another, are H or $C_1$–$C_{12}$alkyl;

$R_3$ and $R_4$, independently of one another, are H, $C_1$–$C_{18}$alkyl or —X—(Z)$_r$—$R_5$;

$R_5$ is a monovalent radical of a sterically hindered amine or of a UV absorber from the class of the 2-hydroxyphenylbenzotriazoles, 2-hydroxyphenylbenzophenones, oxalanilides or 2-hydroxyphenyl-4,6-diaryltriazines or a radical of a sterically hindered phenol; and $R_8$ is H, $C_1$–$C_{18}$alkyl, $C_7$–$C_{11}$phenylalkyl, $C_2$–$C_6$alkoxyalkyl or $C_5$–$C_{12}$cycloalkyl.

The index y corresponds to the valency of R. If r is 0 and X is a direct bond, R in formula I bonds directly to the oxazoline ring.

If y is greater than 1, then r, X and Z can have identical or different meanings.

R or $R_5$ is an organic radical comprising at least one molecular fragment of the abovementioned type which is effective as stabilizer, the radical as a whole containing in general from 9 to about 200, in most cases from 9 to 50 carbon atoms and from 1 to about 40, in most cases from 1 to 10 heteroatoms, and the radical containing at least 1 nitrogen or oxygen atom and further heteroatoms preferably being selected from the atoms N, O, S and Cl; especially nitrogen and/or oxygen.

In the compounds of the formula I, heteroatoms generally bond to carbon and/or hydrogen, unless sulfo groups of the type S—S, SO, $SO_2$ or $SO_3$ are involved;

heteroatoms are usually in the form of ether, hydroxyl, ester, carboxyl, amino, amido, thio or sulfone groups, in particular as ether, hydroxyl, ester, amino or amido groups.

If Z is a hydrocarbon radical which is interrupted in the aliphatic moiety by one or more divalent functional groups, then it is preferably a hydrocarbon radical which is substituted by OH or interrupted by a functional group in a carbon-carbon single bond; preferred functional groups are —O—, —$NR_8$—, —S—, —$SO_2$—, —CO—, —CONH— and —COO—.

R comprises molecular fragments of the sterically hindered amine, 2-hydroxyphenylbenzotriazole, 2-hydroxyphenylbenzophenone, oxalanilide, 2-hydroxyphenyl-4,6-diaryltriazine, or sterically hindered phenol type;

particularly suitable molecular fragments of the sterically hindered amine type are those comprising one or more groups of the formula II

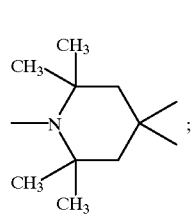

(II)

molecular fragments effective as UV absorbers from the class of the 2-hydroxyphenyl-benzotriazoles comprise one or more groups of the formula III

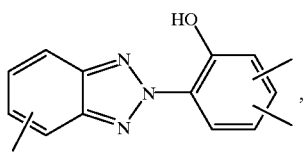

those from the class of the 2-hydroxyphenylbenzophenones comprise one or more groups of the formula IV

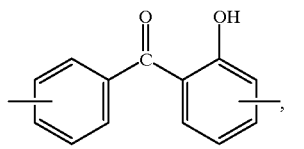

those from the class of the oxalanilides comprise one or more groups of the formula V

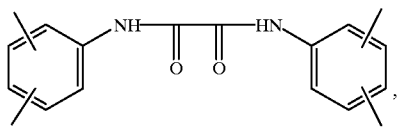

those from the class of the 2-hydroxyphenyl-4,6-diaryltriazines comprise one or more groups of the formula VI

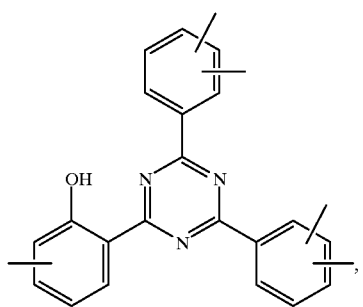

molecular fragments from the class of the sterically hindered phenols comprise one or more groups of the formula VII

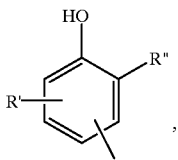

in which R' is $C_1$–$C_{18}$alkyl or cyclohexyl, especially methyl or tert-butyl, and R'' is tert-$C_4$–$C_{18}$alkyl or cyclohexyl, especially tert-butyl;
the formulae depicted can be monovalent or multivalent, in which case surplus bonds are satisfied by H, OH, halogen or a monovalent aliphatic, aromatic or mixed aromatic-aliphatic $C_1$–$C_{18}$ hydrocarbon radical or an aliphatic or mixed-aromatic-aliphatic $C_1$–$C_{18}$ hydrocarbon radical which is interrupted in the aliphatic moiety by one or more divalent functional groups and/or is attached via a divalent functional group, possible functional groups being —O—, —$NR_8$—, —S—, —SO—, —$SO_2$—, —CONH—, —CO— or —COO—. Surplus bonds are preferably satisfied by H, OH, halogen, $C_1$–$C_{18}$alkyl, $C_1$–$C_{18}$alkoxy, phenyl, $C_7$–$C_{11}$alkylphenyl, $C_7$–$C_{11}$phenylalkyl, $C_7$–$C_{11}$phenylalkoxy, $C_5$–$C_{12}$cycloalkyl or $C_5$–$C_{12}$cycloalkoxy.

For example, radicals of the 2-hydroxyphenyl-4,6-diaryltriazine type can be monovalent, divalent or else trivalent and, inter alia, can have the formulae

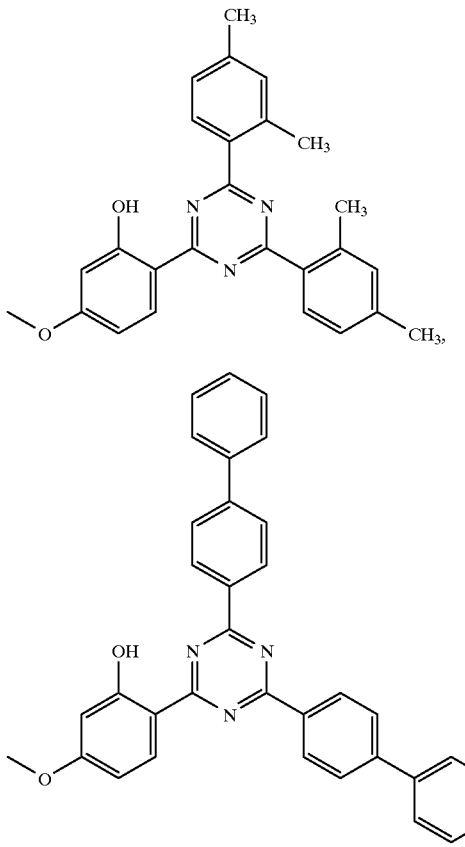

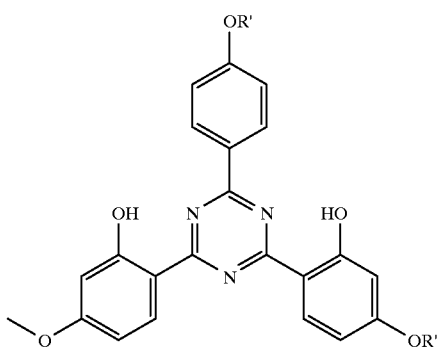

-continued

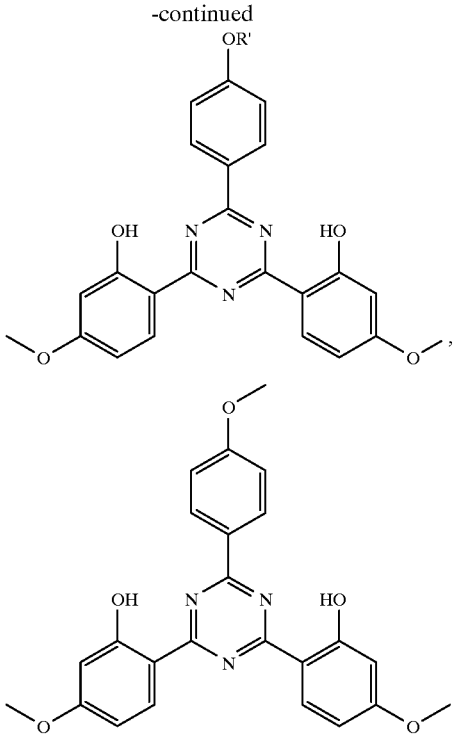

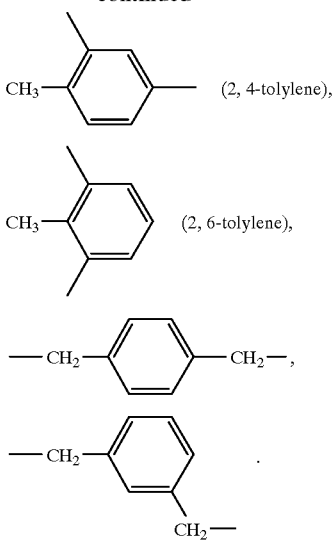

where R' is, for example, $C_1$–$C_{18}$alkyl.

An aliphatic $C_1$–$C_{18}$ hydrocarbon radical is one which contains no aromatic groups (aryl); cycloaliphatic hydrocarbon radicals are included. Thus a monovalent aliphatic $C_1$–$C_{18}$ hydrocarbon radical is, for example, $C_1$–$C_{18}$alkyl or $C_2$–$C_{18}$alkenyl; a divalent aliphatic $C_1$–$C_{18}$ hydrocarbon radical is, for example, $C_1$–$C_{18}$alkylene or $C_2$–$C_{18}$alkenylene; a trivalent aliphatic $C_1$–$C_{18}$ hydrocarbon radical is, for example, $C_1$–$C_{18}$alkanetriyl or $C_4$–$C_{18}$alkenetriyl.

A mixed aromatic-aliphatic radical contains at least 7 carbon atoms and includes those hydrocarbon radicals which contain both at least one saturated aliphatic unit and one aryl unit, the bond or bonds being localized either on the aryl unit or on an aliphatic unit or on the aryl unit and on an aliphatic unit. Aryl units are essentially phenyl, phenylene, biphenyl, biphenylene, naphthyl or naphthylene. These radicals therefore include, for example, those of the formulae

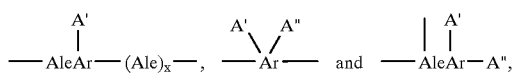

in which Ar is in each case an aryl unit as indicated, Ale is $C_1$–$C_6$alkylene, A' and A" independently of one another are H or $C_1$–$C_6$alkyl and the index x is 0 or 1, with the proviso that the sum of the carbon atoms is at least 7, preferably from 7 to 18.

Preferred divalent radicals of this kind include

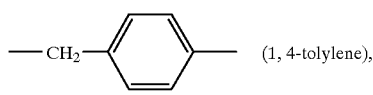

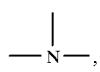

A cycloaliphatic hydrocarbon radical is in most cases saturated and preferably contains 5–12 carbon atoms; this includes, for example $C_5$–$C_{12}$cycloalkyl and also mixed cycloalkyl/alkyl radicals with the appropriate number of carbon atoms, for example alkyl-substituted cycloalkyl, cycloalkyl-substituted alkyl and alkyl interrupted by cycloalkyl.

Preferred compounds of the formula I are those in which

R, if y is 1, is a monovalent radical $Z_1$—$R_5$,

R, if y is 2, is a divalent radical $Z_2$—$R_6$, and

R, if y is 3, is a trivalent radical $Z_3$—$R_7$; and $Z_1$ comprises the meanings given for X—(Z)$_r$;

$Z_2$ is divalent or trivalent and as a divalent radical comprises the meanings indicated for $Z_1$ or is a trivalent aliphatic or mixed aromatic-aliphatic $C_1$–$C_{18}$ hydrocarbon radical or an aliphatic or mixed aromatic-aliphatic $C_1$–$C_{18}$ hydrocarbon radical which is interrupted in the aliphatic moiety by one or more divalent functional groups, in each case in a carbon-carbon single bond, and/or is substituted by OH and/or is attached via a divalent or trivalent functional group, or is

—N—, possible functional groups being —O—, —NR$_8$—, —S—, —SO—, —SO$_2$—, —CO—, —CONH— or —COO—;

$Z_3$ is divalent, trivalent or tetravalent and comprises the meanings indicated for $Z_2$ or is a tetravalent aliphatic or mixed aliphatic-aromatic $C_1$–$C_{18}$ hydrocarbon radical or a tetravalent aliphatic or mixed aromatic-aliphatic $C_1$–$C_{18}$ hydrocarbon radical which is interrupted in the aliphatic moiety by one or more divalent functional groups, in each case in a carbon-carbon single bond, and/or is substituted by OH and/or is attached via a divalent functional group, possible functional groups being —O—, —NR$_8$—, —S—, —SO—, —SO$_2$—, —CO—, —CONH— or —COO—;

$R_5$ has one of the formulae
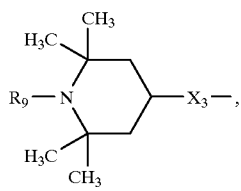
(IIa)
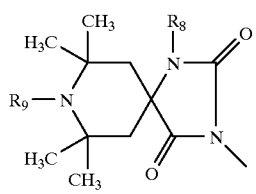
(IIb)
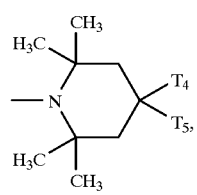
(IIc)
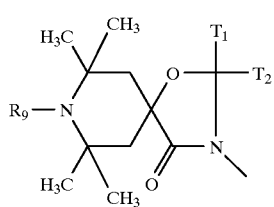
(IId)
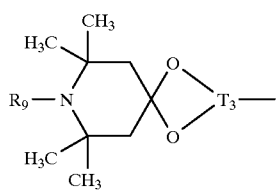
(IIe)
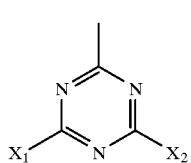
(IIf)
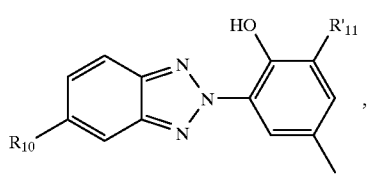
(IIIa)
-continued
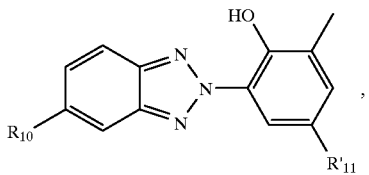
(IIIb)
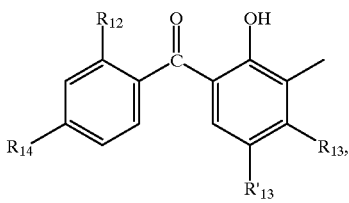
(IVa)
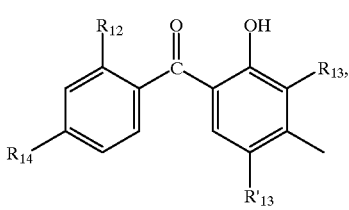
(IVb)
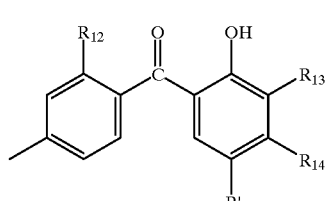
(IVc)
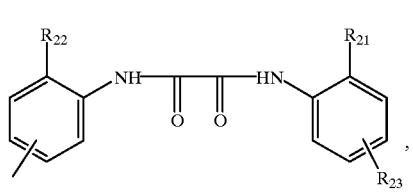
(Va)
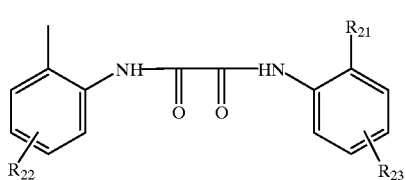
(Vb)
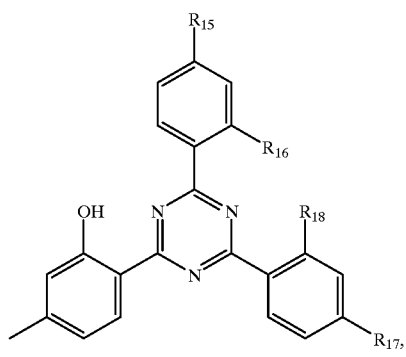
(VIa)

(VIb)
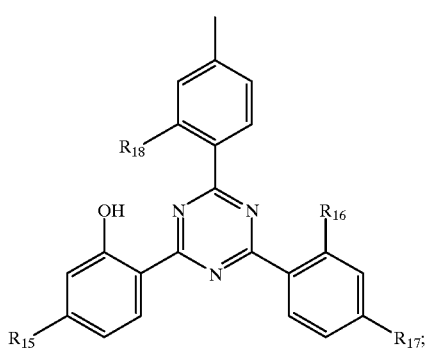
$R_6$ has one of the meanings indicated for $R_5$ or has one of the formulae
(IIIc)
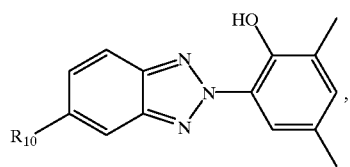
(IVd)
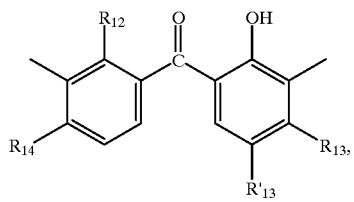
(IVe)
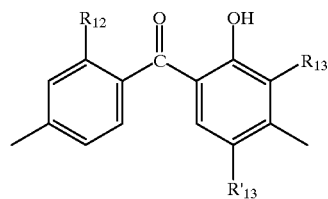
(Vc)
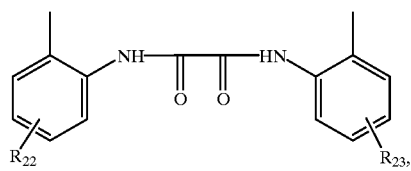
(Vd)
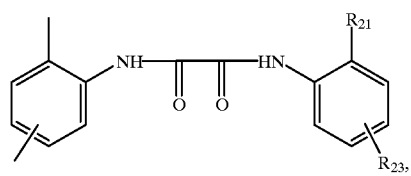
(Ve)
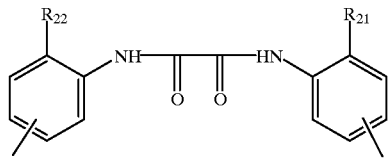
(VIc)
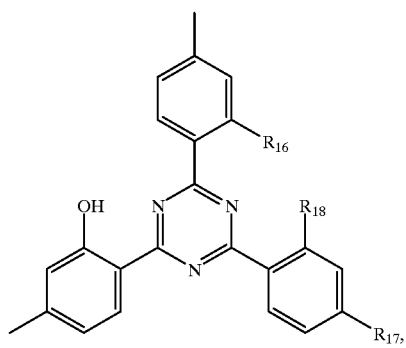
(VId)
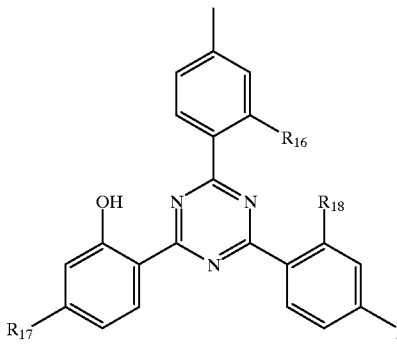
(VIIa)
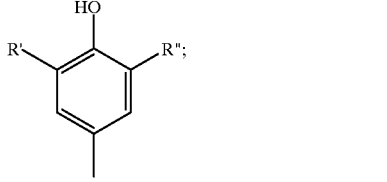
$R_7$ has one of the meanings indicated for $R_5$ or $R_6$ or has the formula
(VIe)
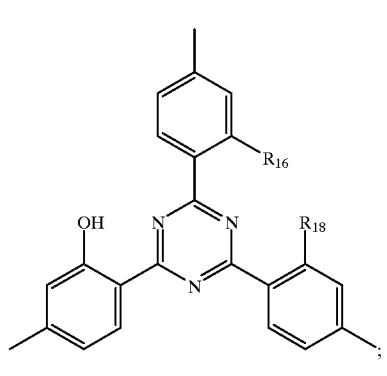

in which

R' is $C_1$–$C_{18}$alkyl or cyclohexyl, especially methyl or tert-butyl, and

R" is tert-$C_4$–$C_{18}$alkyl or cyclohexyl, especially tert-butyl;

$R_8$ is H, $C_1$–$C_{18}$alkyl, $C_7$–$C_{11}$phenylalkyl, $C_2$–$C_6$alkoxyalkyl or $C_5$–$C_{12}$cycloalkyl;

$R_9$ is hydrogen, oxyl, hydroxyl, $C_1$–$C_{18}$alkyl, $C_3$–$C_8$alkenyl, $C_3$–$C_8$alkynyl, $C_7$–$C_{12}$aralkyl, $C_1$–$C_{18}$alkoxy, $C_5$–$C_{12}$cycloalkoxy, $C_7$–$C_9$phenylalkoxy, $C_1$–$C_8$alkanoyl, $C_3$–$C_5$alkenoyl, $C_1$–$C_{18}$alkanoyloxy, benzyloxy, glycidyl or a group —$CH_2CH(OH)$—G, in which G is hydrogen, methyl or phenyl, with $R_9$ preferably being H, $C_1$–$C_4$alkyl, $C_3$–$C_4$alkenyl, $C_3$–$C_4$alkynyl, allyl, benzyl, cyclohexyloxy, $C_1$–$C_{12}$alkoxy, acetyl or acryloyl;

$R_{10}$ is H, Cl, $C_1$–$C_4$alkyl or $C_1$–$C_4$alkoxy;

$R_{11}$ is $C_1$–$C_{12}$alkyl;

$R'_{11}$ is H or $C_1$–$C_{12}$alkyl;

$R_{12}$ is H or OH;

$R_{13}$ is H, Cl, OH or $C_1$–$C_{18}$alkoxy;

$R'_{13}$ is H, Cl or $C_1$–$C_4$alkyl;

$R_{14}$ is H, Cl, OH or $C_1$–$C_{18}$alkoxy;

$R_{15}$ and $R_{17}$, independently of one another, are H, OH, Cl, CN, phenyl, $C_1$–$C_6$alkyl, $C_1$–$C_{18}$alkoxy, $C_4$–$C_{22}$alkoxy which is interrupted by O and/or substituted by OH, or are $C_7$–$C_{14}$phenylalkoxy; and $R_{16}$ and $R_{18}$, independently of one another, are H, OH, Cl, $C_1$–$C_6$alkyl or $C_1$–$C_6$alkoxy;

$R_{19}$ and $R'_{19}$, independently of one another, have one of the meanings indicated for $R_8$ or together form tetramethylene or -oxamethylene or pentamethylene or -oxamethylene;

$R_{20}$ is $C_1$–$C_{18}$alkyl, $C_2$–$C_4$alkenyl or phenyl;

$R_{21}$, $R_{22}$ and $R_{23}$, independently of one another, are H, $C_1$–$C_{18}$alkyl or $C_1$–$C_{18}$alkoxy;

$T_1$ and $T_2$, independently of one another, are hydrogen, $C_1$–$C_{18}$alkyl, phenyl-$C_1$–$C_4$alkyl or unsubstituted or halogen- or $C_1$–$C_4$alkyl-substituted phenyl or naphthyl or $T_1$ and $T_2$, together with the carbon atom connecting them, form a $C_5$–$C_{12}$cycloalkane ring, $T_3$ is $C_2$–$C_8$alkanetriyl, especially

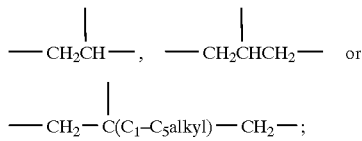

or $T_4$ is hydrogen, $C_1$–$C_{18}$alkoxy, $C_3$–$C_8$alkenyloxy or benzyloxy, and $T_5$ has the same meaning as $T_4$, or $T_4$ and $T_5$ together are —O—$C_2$–$C_8$alkylene-O—, or $T_5$, if $T_4$ is hydrogen, is —OH or —$NR_8$—CO—$R_{20}$;

$X_1$ is a group of the formula IIa and $X_2$ has the same meaning as $X_1$ or is $C_1$–$C_{18}$alkoxy or —$NR_{19}R'_{19}$;

$X_3$ is —$NR_8$—, —$NX_6$— or —O—, or is a radical of the formula —O—CO—$X_5$—CO—O—$X_6$, where $X_5$ is $C_1$–$C_{12}$alkanetriyl and $X_6$ is a radical of the formula

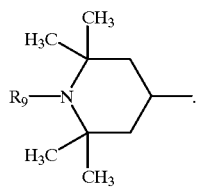

In the novel compounds, $R_1$ and $R_2$, independently of one another, are preferably H or $C_1$–$C_{12}$alkyl; and $R_3$ and $R_4$, independently of one another, are preferably H, $C_1$–$C_{18}$alkyl or —$Z_1$—$R_5$, especially H or $C_1$–$C_{12}$alkyl.

If $Z_1$, $Z_2$ or $Z_3$, when r=0, are a direct bond, then monovalent $R_5$, $R_6$ and/or $R_7$ bond directly to X. If X and $Z_1$, $Z_2$ or $Z_3$ in each case are a direct bond, then monovalent $R_5$, $R_6$ and/or $R_7$ bond directly to Z (if r=1) or to the carbon atom of the oxazoline ring (if r=0).

Among these compounds, preference is given to those in which $R_5$, $R_6$ and/or $R_7$ are not attached directly to the carbon atom of the oxazoline ring.

$R_8$ is preferably $C_3$–$C_{12}$alkyl and especially hydrogen.

$R_9$ as $C_3$–$C_8$alkynyl is preferably propargyl.

$R_9$ as aralkyl is in most cases $C_7$–$C_{12}$phenylalkyl and preferably phenethyl, especially benzyl or cumyl.

$R_9$ as $C_2$–$C_{18}$alkanoyl is typically propionyl, butyryl, octanoyl and, preferably, acetyl; and as $C_3$–$C_6$alkenoyl is especially acryloyl or methacryloyl.

A preferred group of compounds of the formula I are those in which r is 0 and X is a direct bond and which have the formulae Ia–Ie.

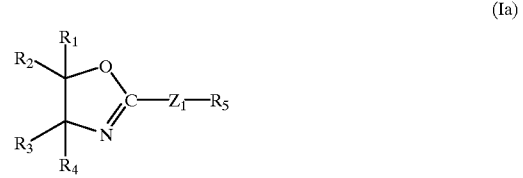

(Ia)

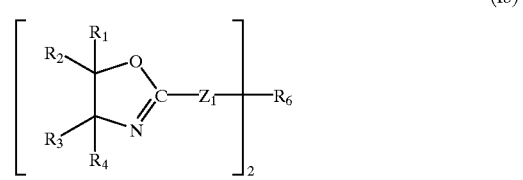

(Ib)

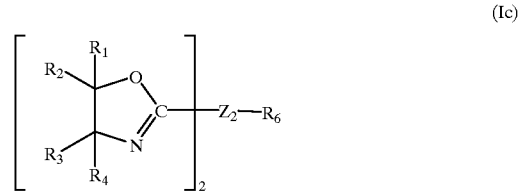

(Ic)

-continued

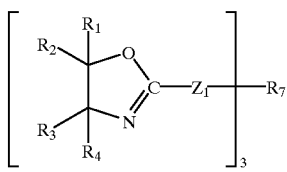
(Id)

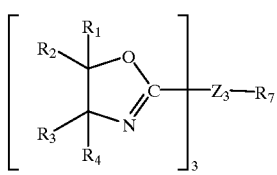
(Ie)

in which

R$_1$ and R$_2$, independently of one another, are H or C$_1$–C$_{12}$alkyl;

R$_3$ and R$_4$, independently of one another, are H, C$_1$–C$_{18}$alkyl or —Z$_1$—R$_5$;

Z$_1$ is phenylene, a divalent group of one of the formulae -phenylene-Z$_4$—, -phenylene-Z$_5$—, —Z$_4$—Z$_5$ or X—Z$_4$—Z$_5$, where Z$_5$ does not bond to the oxazoline ring;

or Z$_1$ has one of the meanings indicated for Z$_4$ or X;

Z$_2$ as trivalent radical is T, T—Z$_5$, T—(Z$_5$)$_2$, X—T, (X)$_2$—T, X—T—Z$_5$, (X)$_2$—T—Z$_5$ or X—T—(Z$_5$)$_2$, where X bonds to the oxazoline ring and Z$_5$ bonds to R$_6$ and T is C$_1$–C$_{12}$alkanetriyl or C$_3$–C$_{12}$alkanetriyl which is interrupted by phenylene, cyclohexylene and/or Z$_5$ and/or is substituted by OH;

Z$_3$ as tetravalent radical is D, D—Z$_5$, D—(Z$_5$)$_2$, D—(Z$_5$)$_3$, X—D, (X)$_2$—D, (X)$_3$—D, X—D—Z$_5$, (X)$_2$—D—Z$_5$, (X)$_3$—D—Z$_5$, X—D—(Z$_5$)$_2$ or X—D—(Z$_5$)$_3$, where X bonds to the oxazoline ring and Z$_5$ bonds to R$_7$ and D is C$_1$–C$_{12}$alkanetetrayl or is C$_3$–C$_{12}$alkanetetrayl which is interrupted by phenylene, cyclohexylene and/or Z$_5$ and/or is substituted by OH;

Z$_4$ is C$_1$–C$_{12}$alkylene or is C$_2$–C$_{12}$alkylene which is interrupted by phenylene, cyclohexylene and/or Z$_5$, and/or is substituted by OH; and Z$_5$ is —O—, —NR$_8$—, —S—, —SO—, —SO$_2$—, —CO—, —CONR$_8$— or —COO—.

Particularly preferred compounds according to the invention are those of the formulae Ia–Id.

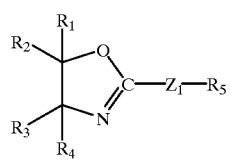
(Ia)

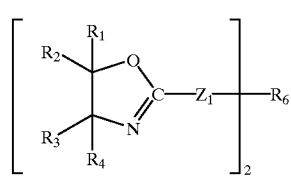
(Ib)

-continued

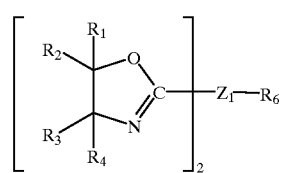
(Ic)

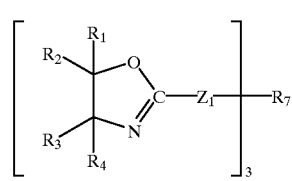
(Id)

in which

R$_3$ and R$_4$, independently of one another, are H or C$_1$–C$_{12}$alkyl;

R$_5$ has one of the formulae

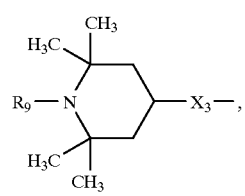
(IIa)

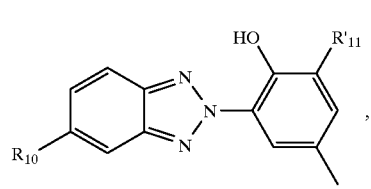
(IIIa)

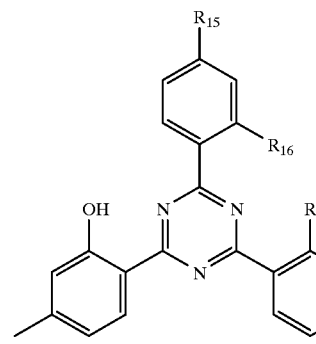
(VIa)

(VIb)

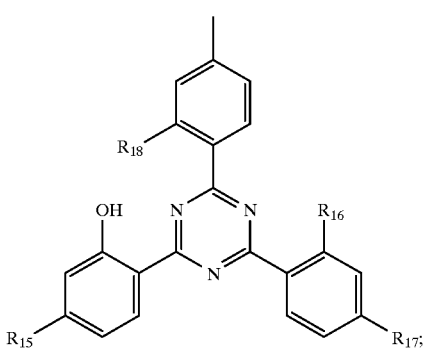

$R_6$ has one of the meanings indicated for $R_5$ or has one of the formulae (VIc)

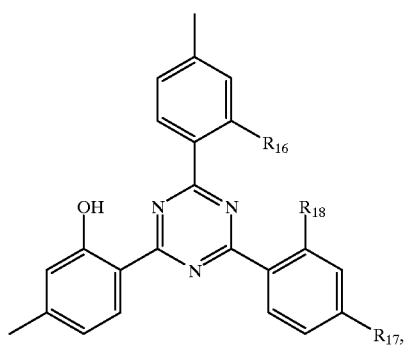

(VId)

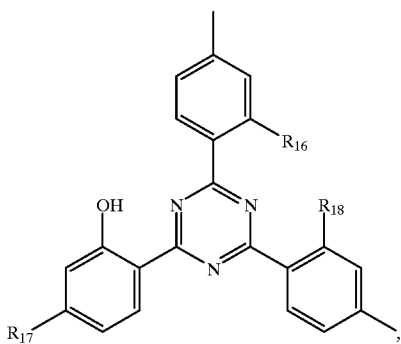

(VIIa)

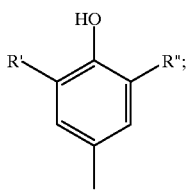

and $R_7$ has the formula (VIe)

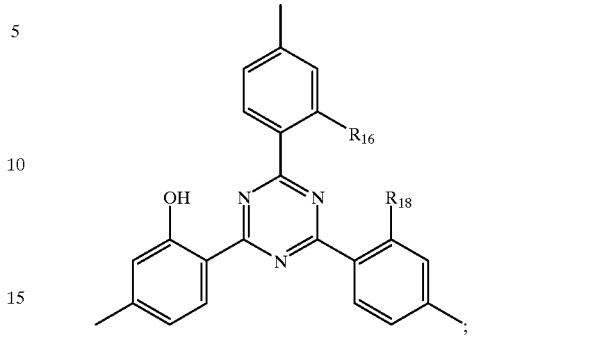

in which
R' is methyl, tert-butyl or cyclohexyl and
R" is tert-butyl or cyclohexyl;
$R_8$ is H, $C_3$–$C_8$alkyl, benzyl or cyclohexyl;
$R_9$ is hydrogen, methyl, $C_6$–$C_{12}$alkoxy or cyclohexyloxy;
$R_{10}$ is H, Cl, methyl or methoxy;
$R_{15}$ and $R_{17}$, independently of one another, are H, OH, Cl, phenyl, methyl, $C_1$–$C_{18}$alkoxy, $C_4$–$C_{22}$alkoxy which is interrupted by O and/or substituted by OH, or are benzyloxy; and
$R_{16}$ and $R_{18}$, independently of one another, are H, OH, Cl, or methyl; and
$X_3$ is —$NR_8$— or —O—;
$Z_1$ is a divalent group of one of the formulae —$Z_4$—$Z_5$ or X—Z—$Z_5$, where $Z_5$ does not bond to the oxazoline ring; or $Z_1$ has one of the meanings indicated for $Z_4$ or X;
$Z_2$ as a trivalent radical is T, T—$Z_5$, T—$(Z_5)_2$, where $Z_5$ bonds to $R_6$ and T is $C_1$–$C_{12}$alkanetriyl or OH-substituted $C_3$–$C_{12}$alkanetriyl;
$Z_3$ as a tetravalent radical is D, D—$Z_5$, D—$(Z_5)_2$ or D—$(Z_5)_3$, where $Z_5$ bonds to $R_7$ and D is $C_1$–$C_{12}$alkanetetrayl or OH-substituted $C_3$–$C_{12}$alkanetetrayl;
$Z_4$ is $C_1$–$C_{12}$alkylene or is $C_3$–$C_{12}$alkylene which is interrupted by phenylene and/or $Z_5$ and/or is substituted by OH; and
$Z_5$ is —O—, —$NR_8$— or —COO—.

The compounds according to the invention can be prepared in analogy to known methods, as are described, for example, by J. A. Frump, Chemical Reviews 71, 483–505 (1971) and in U.S. Pat. No. 4,843,087, U.S. Pat. No. 5,039,781, EP-A-8507, and V. I. Kelarev et al., Khim. Geterotsiklicheskikh Soedinenii, 889 (1984). For example, a compound of the formula I can be obtained, with construction of the oxazoline ring, from a compound of the formula

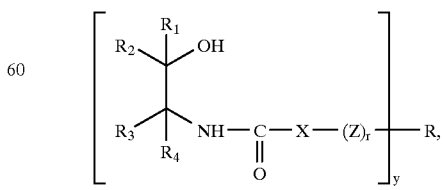

in which R, $R_1$—$R_4$, X, Z, r and y have the meanings indicated for formula I by reaction with thionyl chloride (see for example method G in the abovementioned publication of J. A. Frump, pp. 487–488).

A further access possibility is the synthesis of an oxazoline derivative of the formula

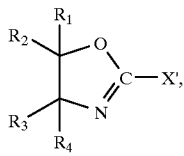

in which X' is an appropriate reactive group such as, for example, $NR_8H$, COCl, COOH, COOR'— in which R' is lower alkyl- or haloalkyl, or the synthesis of an oxazoline derivative of the formula

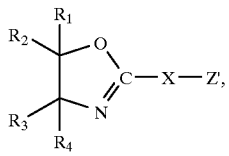

in which $R_1$—$R_4$ and X each have the meanings indicated for formula I and Z' differs from Z of formula I in that Z' carries, instead of the bond to the radical R, a suitable reactive group such as, for example, halogen, COOR', CHO or COR', in which R' is in each case lower alkyl, in accordance with one of the known methods or in analogy thereto and its subsequent reaction with an appropriate co-reactant from the class of the sterically hindered amines, 2-hydroxyphenylbenzotriazoles, 2-hydroxyphenylbenzophenones, oxalanilides or 2-hydroxyphenyl-4,6-diaryltriazines or the sterically hindered phenols, to form the desired compound.

If $R_3$ and/or $R_4$ in the target compound of the formula I are a radical —X—$(Z)_r$—$R_5$, then it is likewise possible first of all to prepare an isolated oxazoline ring analogous to the above formulae but containing $R'_3$ and/or $R'_4$ instead of $R_3$ and/or $R_4$ respectively, in the meaning given with $R'_3$ and $R'_4$ as reactive radicals X' or —X—Z' (meanings as indicated above) and to react this product as set out above to give the end product.

The novel compounds can be employed with advantage for stabilizing organic material against the damaging effect of light, oxygen and/or heat. They are notable for high substrate compatibility and good persistence in the substrate.

Examples of materials to be stabilized in accordance with the invention are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1 -ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EM), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/ butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention therefore also provides compositions comprising

A) an organic material which is sensitive to oxidative, thermal and/or actinic degradation, and B) at least one compound of the formula I, and provides for the use of compounds of the formula I for stabilizing organic material against oxidative, thermal or actinic degradation.

The invention likewise comprises a method of stabilizing organic material against thermal, oxidative and/or actinic degradation, which comprises adding to this material at least one compound of the formula I.

Of particular interest is the use of compounds of the formula I as stabilizers in synthetic organic polymers, especially thermoplastic polymers, and corresponding compositions.

The organic materials to be protected are preferably natural, semisynthetic or, preferably, synthetic organic materials. Particular preference is given to synthetic organic polymers or mixtures of such polymers, especially thermoplastic polymers such as polyolefins or styrene copolymers, for example those specified in the above list under 1., 2., 3., 6. and 7., especially ABS, polyethylene and polypropylene (PP), and coating compositions.

In general the compounds of the formula I are added to the material to be stabilized in amounts of from 0.1 to 10%, preferably from 0.01 to 5%, in particular from 0.01 to 2% (based on the material to be stabilized). Particular preference is given to the use of the novel compounds in amounts of from 0.05 to 1.5%, especially from 0.1 to 0.5%.

Incorporation into the materials can be effected, for example, by mixing in or applying the compounds of the formula I and, if desired, further additives by the methods which are customary in the art. Where polymers are involved, especially synthetic polymers, incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the compounds of the formula I into polymers is to add them before, during or directly after the polymerization of the corresponding monomers or prior to crosslinking. In this context the compound of the formula I can be added as it is or else in encapsulated form (for example in waxes, oils or polymers). In the case of addition prior to or during the polymerization, the compounds of the formula I can also act as a regulator of the chain length of the polymers (chain terminator).

The compounds of the formula I can also be added in the form of a masterbatch containing said compound in a concentration, for example, of from 2.5 to 25% by weight to the polymers that are to be stabilized.

The compounds of the formula I can judiciously be incorporated by the following methods:

as emulsion or dispersion (e.g. to latices or emulsion polymers), as a dry mixture during the mixing in of additional components or polymer mixtures, by direct introduction into the processing apparatus (e.g. extruders, internal mixers, etc), as solution or melt.

With particular advantage, the novel compound is added to a thermoplastic polymer prior to its processing at elevated temperature, as is frequently carried out, for example, by means of an extruder.

The novel 2-oxazoline stabilizers are capable of binding reactively to the organic material that is to be stabilized. This takes place in particular on heating of a thermoplastic polymer to which compounds of the formula I have been added to processing temperature, or by addition to organic material which contains functional groups which are effective as acids, especially proton-donating functional groups, for example —COOH, —SO$_3$H, phenolic OH groups and/or SH groups.

The invention therefore also provides a method for stabilizing thermoplastic polymers, especially those containing functional groups of the type —COOH, —SO$_3$H, phenolic OH groups and/or SH groups, against thermal, oxidative or/and actinic degradation, which comprises admixing to these polymers at least one compound of the formula I and heating the mixture, for example by extrusion.

The invention additionally provides a thermoplastic polymer, especially one comprising functional groups of the type —COOH, —SO$_3$H, phenolic OH groups and/or SH groups, which comprises a compound of the formula I in bound form, especially after reactive extrusion.

Correspondingly modified polymers which contain a relatively high amount of the novel oxazoline additive in bound form, for example from 2.5 to 25% by weight, can also be used themselves as stabilizers. The invention therefore additionally embraces the use of the polymers modified in accordance with the invention as stabilizers of organic material against thermal, oxidative and/or actinic degradation.

The invention additionally provides a correspondingly modified thermoplastic polymer comprising, instead of the compound of the formula I, a compound of the formula X in bound form

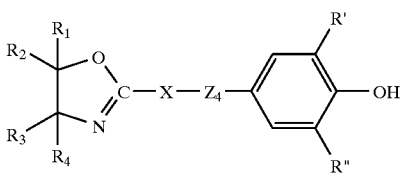

(X)

in which

R₁, R₂, R₃ and R₄, independently of one another, are H or C₁–C₁₂alkyl, especially H;

R' is methyl, tert-butyl or cyclohexyl, especially methyl or tert-butyl, and

R" is tert-butyl or cyclohexyl, especially tert-butyl;

Z₄ is C₁–C₁₂alkylene; or is C₃–C₁₂alkylene interrupted by phenylene, —O—, —COO— and/or —CONH—; in particular is C₂–C₈alkylene; and X is a direct bond or —NR₈—, —CO—, —CONH— or —COO—, in particular a direct bond, where R₈ is H, C₃–C₈alkyl, benzyl or cyclohexyl;

and for its use as stabilizer for organic material against thermal, oxidative and/or actinic degradation, and a corresponding method of stabilization.

The invention thus additionally comprises a method of stabilizing a thermoplastic polymer, especially one comprising functional groups of the type —COOH, —SO₃H, phenolic OH groups and/or SH groups, against thermal, oxidative and/or actinic degradation, which comprises admixing to this polymer at least one compound of the formula X and heating the mixture, for example by extrusion.

The compound of the formula X is preferably employed in the same proportion as indicated for the compounds of the formula I.

Novel polymer compositions can be employed in various forms and/or processed to give various products, for example as (to give) films, fibres, tapes, moulding compositions, profiles, or as binders for coating materials, adhesives or putties.

In addition to the compounds of the formula I the novel compositions may as additional component C comprise one or more conventional additives such as, for example, those indicated below.

The conventional additives are judiciously employed in amounts of 0.1–10% by weight, for example 0.2–5% by weight, based on the material to be stabilized.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butyl phenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis[3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzyl mercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6- trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic Acid (Vitamin C)

1.19. Aminic antioxidants, for example N,N'-di-isopropyl-p-phenylenediamine, N,N'-di-secbutyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N', N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tertoctyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- and dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

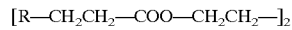

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl)n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis-(2,2,6,6-tetramethyl-4-piperidyl)-1, 2,3,4-butane-tetracarboxylate, 1,1'-(1,2-ethanediyl)-bis-(3, 3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2, 4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4, 6-trichloro-1,3,5-triazine as well as 4-butylamino-2,2,6,6-tetramethylpiperidine (CAS Reg. No. [136504-96-6]); N-(2, 2,6,6-tetramethyl-4-piperidyl)-n-dodecylsuccinimid, N-(1, 2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl) hexamethylenediamine, diester of 4-methoxymethylenemalonic acid with 1,2,2,6,6-pentamethyl-4-hydroxypiperidine, poly[methylpropyl3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyioxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2- hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12 H-di-benz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite.

Especially preferred are the following phosphites:

Tris(2,4-di-tert-butylphenyl)phosphite (Irgafos®168, Ciba-Geigy), tris(nonylphenyl)phosphite,

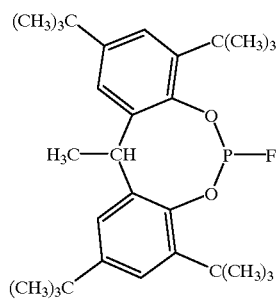

(A)

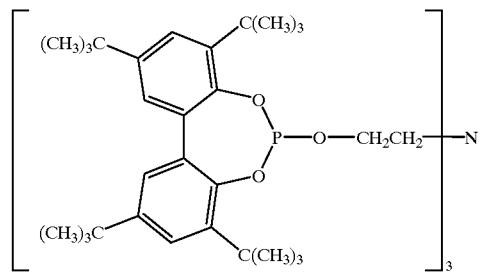

(B)

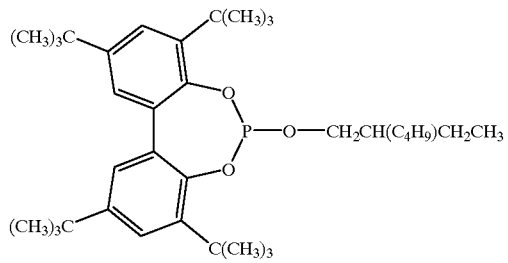

(C)

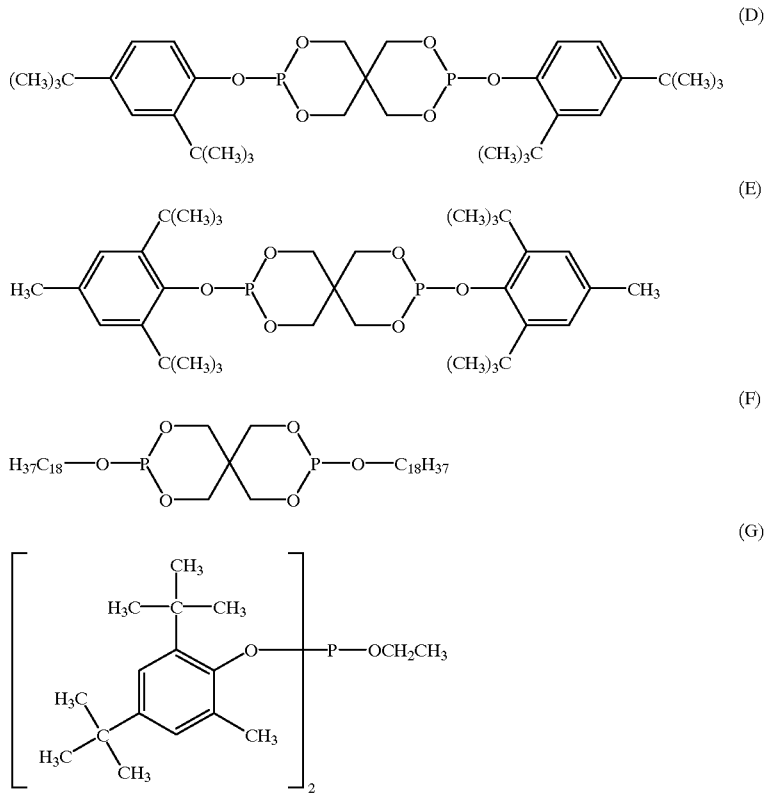

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[(2-acetoxyethoxy)phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-([2- hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

Also of particular interest is the use of the novel compounds of the formula I as stabilizers for coatings, for example for paints. The invention therefore also provides those compositions whose component A is a film-forming binder (coating composition).

The novel coating composition preferably contains, per 100 parts by weight of solid binder A, 0.01–10 parts by weight of B, in particular 0.05–10 parts by weight of B, especially 0.1–5 parts by weight of B.

Multicoat systems are also possible here, in which case the concentration of the compound of the formula I (component B) in the topcoat can be higher, for example from 1 to 15 parts by weight of B, especially 3–10 parts by weight of B per 100 parts by weight of solid binder A.

The use of the compound of the formula I as stabilizer in coatings brings the additional advantage that delamination, i.e. the flaking of the coating from the substrate, is prevented. This advantage is particularly marked in the case of metallic substrates, and also in the case of multicoat systems on metallic substrates.

Suitable binders (component A) are in principle all those which are customary in the art, for example those as described in Ullmann's Encyclopedia of Industrial Chemistry, 5th Edition, Vol. A18, pp. 368–426, VCH, Weinheim 1991. The substance involved is generally a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component A can be a cold-curable or a hot-curable binder, the addition of a curing catalyst possibly being of advantage. Examples of suitable catalysts which accelerate the curing of the binder are described in Ullmann's Encyclopedia of Industrial Chemistry, Vol. A18, S.469, VCH Verlagsgesellschaft, Weinheim 1991.

Preference is given to coating compositions in which component A is a binder comprising a functional acrylate resin and a crosslinker.

Examples of coating compositions with specific binders are:

1. paints based on cold- or hot-crosslinkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking, if desired with addition of a melamine resin;
4. one-component polyurethane paints based on aliphatic or aromatic urethanes or polyurethanes and hydroxyl group containing acrylate, polyester or polyether resins;
5. one-component polyurethane paints based on aliphatic or aromatic urethaneacrylates or polyurethaneacrylates having free amino groups within the urethane structure and melamine resins or polyether resins, if necessary with curing catalyst;
6. two-component paints based on (poly)ketimines and aliphatic or aromatic isocyanates, isocyanurates or polyisocyanates;
7. two-component paints based on (poly)ketimines and an unsaturated acrylate resin or a polyacetoacetate resin or a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and acrylate resins containing anhydride groups, or unsaturated acrylate resins, or aliphatic or aromatic isocyanates, isocyanurates or polyisocyanates;
12. two-component paints based on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins.

The novel coating compositions can also be radiation-curable. In this case, the binder essentially comprises monomeric or oligomeric compounds containing ethylenically unsaturated bonds (prepolymers) which are cured, after application, by UV radiation or electron beams, i.e. are converted into a crosslinked, high molecular mass form. Use is often made of photoinitiators such as, for example, benzophenone, benzophenone derivatives, acetophenone, acetophenone derivatives such as, for example, α-hydroxycycloalkyl phenyl ketones, dialkoxyacetophenones, α-hydroxy- or α-aminoacetophenones, 4-aroyl-1,3-dioxolanes, benzoin alkyl ethers and benzil ketals, monoacylphosphine oxides, bisacylphosphine oxides, ferrocenes or titanocenes. Corresponding systems are described in the abovementioned publication Ullmann's Encyclopedia of Industrial Chemistry, 5th ed., Vol. A18, pp. 451–453. In radiation-curable coating compositions the compounds of the formula I may be employed even without the addition of sterically hindered amines.

In addition to components A and B, the novel coating composition preferably comprises, as component C, a light stabilizer of the sterically hindered amine, 2-(2-hydroxyphenyl)-1,3,5-triazine and/or 2-hydroxyphenyl-2H-benztriazole type, for example as mentioned in the above list under items 2.1, 2.6 and 2.8. Of particular industrial interest in this context is the addition of 4,6-diaryl 2-monoresorcinyl-1,3,5-triazines and/or 2-hydroxyphenyl-2H-benzotriazoles.

In order to achieve maximum light stability it is of particular interest to add sterically hindered amines as mentioned in the above list under 2.6. The invention therefore also provides a coating composition which, in addition to components A and B, comprises a light stabilizer of the sterically hindered amine type as component C.

This is preferably a 2,2,6,6-tetraalkylpiperidine derivative comprising at least one group of the formula

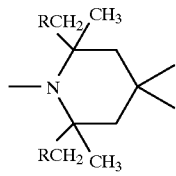

in which R is hydrogen or methyl, especially hydrogen.

Component C is preferably used in an amount of 0.05–5 parts by weight per 100 parts by weight of the solid binder.

Examples of tetraalkylpiperidine derivatives that can be used as component C are given in EP-A-356677, pages 3–17, sections a) to f). Those sections of this EP-A are regarded as part of the present description. It is particularly expedient to employ the following tetraalkylpiperidine derivatives:

bis(2,2,6,6-tetramethylpiperidin-4-yl)succinate,
bis(2,2,6,6-tetramethylpiperidin-4-yl)sebacate,
bis(1,2,2,6,6-pentamethylpiperidin-4-yl)sebacate,
di(1,2,2,6,6-pentamethylpiperidin-4-yl)butyl-(3,5-di-tert-butyl-4hydroxybenzyl)malonate,
bis(1-octyloxy-2,2,6,6-tetramethylpiperidin-4-yl)sebacate,
tetra(2,2,6,6-tetramethylpiperidin-4-yl)butane 1,2,3,4-tetracarboxylate,
tetra(1,2,2,6,6-pentamethylpiperidin-4-yl)butane 1,2,3,4-tetracarboxylate,
2,2,4,4-tetramethyl-7-oxa-3,20-diaza-21-oxo-dispiro [5.1.11.2]heneicosane,
8-acetyl-3-dodecyl-1,3,8-triaza-7,7,9,9-tetramethylspiro[4,5]decane-2,4-dione,
or a compound of the formulae

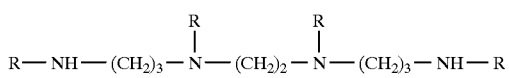

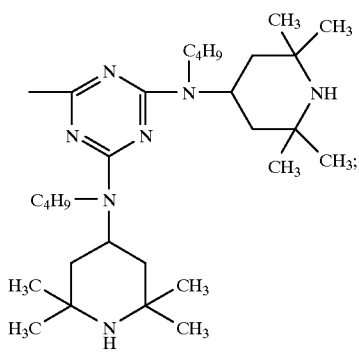

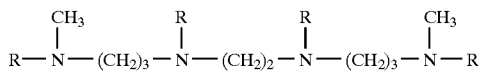

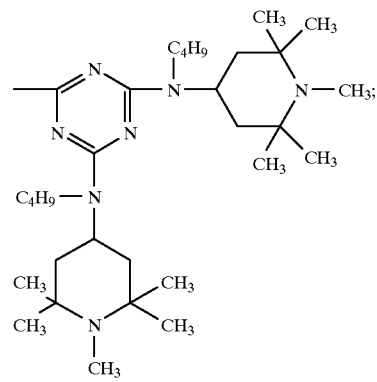

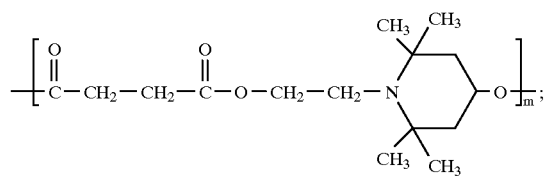

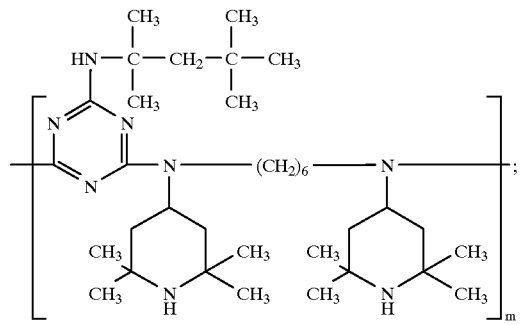

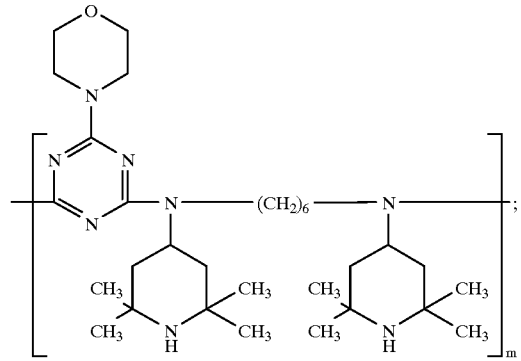

-continued

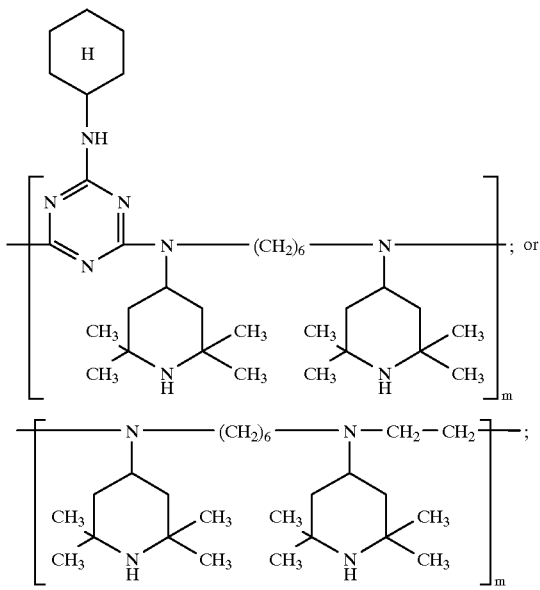

in which m is 5–50.

In addition to components A, B and, if used, C, the coating composition can comprise further components, examples being solvents, pigments, dyes, plasticizers, stabilizers, thixotropic agents, drying catalysts and/or levelling assistants. Examples of possible components are those as described in Ullmann's Encyclopedia of Industrial Chemistry, 5th Edition, Vol. A18, pp. 429–471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr or organometallic compounds such as, for example, organotin compounds.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalysts used can also be phosphines, for example triphenylphosphine.

The novel coating compositions may also be radiation-curable coating compositions. In this case the binder consists essentially of monomeric or oligomeric compounds having ethylenically unsaturated bonds, which following application are cured—i.e. converted to a crosslinked, high molecular mass form—by means of actinic radiation. Where the system involved is a UV curing system it generally comprises, in addition, a photoinitiator. Corresponding systems are described in the abovementioned publication, Ullmann's Encyclopedia of Industrial Chemistry, 5th ed., Vol. A18, pages 451–453. In radiation-curable coating compositions the novel stabilizer mixtures can be employed even without the addition of sterically hindered amines.

The novel coating compositions can be applied to any desired substrates, for example to metal, wood, plastic or ceramic materials. They are preferably used as a topcoat in the painting of automobiles. Where the topcoat comprises two layers, of which the lower layer is pigmented and the upper layer is not pigmented, the novel coating composition can be used for the top or bottom layer or for both layers, but preferably for the upper layer.

The novel coating compositions can be applied to the substrates by the customary techniques, for example by spreading, spraying, curtain coating, dipping or electrophoresis; see also Ullmann's Encyclopedia of Industrial Chemistry, 5th ed., Vol. A18, pp. 491–500.

Depending on the binder system, the coatings can be cured at room temperature or by heating. The coatings are preferably cured at 50–150° C., powder coatings also at higher temperatures.

The coatings obtained in accordance with the invention have excellent resistance to damaging effects of light, oxygen and heat; particular mention should be made of the good light stability and weathering resistance of the resulting coatings, for example paints.

The invention therefore also provides a coating, especially a paint, which has been stabilized against the damaging effects of light, oxygen and heat by adding a compound of the formula I. The paint is preferably a topcoat for automobiles. The invention additionally comprises a process for stabilizing a coating based on organic polymers against damage by light, oxygen and/or heat, which comprises admixing to the coating composition a compound of the formula I, and the use of compounds of the formula I in coating compositions as stabilizers against damage by light, oxygen and/or heat.

The coating compositions can comprise an organic solvent or solvent mixture in which the binder is soluble. However, the coating composition can also be an aqueous solution or dispersion. The vehicle can also be a mixture of an organic solvent and water. The coating composition can be a high-solids paint or may be free from solvent (e.g. powder coating).

The pigments can be inorganic, organic or metallic pigments. The novel coating compositions preferably contain no pigments and are used as clearcoat.

Likewise preferred is the use of the coating composition as a topcoat for applications in the automobile industry, especially as pigmented or unpigmented topcoat of the paint system. However, use for underlying layers is also possible.

The examples below illustrate the invention further. All parts or percentages, in the examples as in the remainder of the description and in the claims, are by weight, unless stated otherwise. In the examples, the following abbreviations are used:
GC: Gas chromatography;
HPLC High-pressure liquid chromatography;
GPC: Gel permeation chromatography;
THF: Tetrahydrofuran;
MALDI: Matrix Assisted Laser Desorption Ionization;
MS: Mass spectrometry;
DSC: Differential thermoanalysis;
$M_n$: Number-average molar mass (units g/mol);
$M_w$: Mass-average molar mass (units g/mol);
H-NMR: Nuclear magnetic resonance of the nuclide $^1$H.
1 torr (=1 mmHg) corresponds to a pressure of about 133 Pa.

A) Preparing the Novel Additives

The compounds of Examples A1 and A2 are starting substances for the novel compound of Example A3.

A1) Methyl 3-(3-benzotriazol-2-yl-5-tert-butyl-4-hydroxyphenyl)propionate (C.A. Reg. No. 84268-33-7) is prepared in accordance with EP-A-57160, Example 3.

A2) Preparation of 3-(3-benzotriazol-2-yl-5-tert-butyl-4-hydroxyphenyl)-N-(2-hydroxyethyl)propionamide (C.A. Reg. No. 96721-34-5)

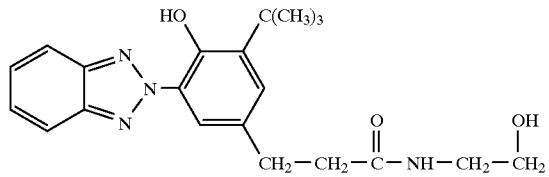

353 g (1.0 mol) of the compound described under A1) and 122 g (2.0 mol) of ethanolamine are charged to a 1.5 l sulfonating flask with stirrer and distillation attachment. The mixture is heated to 140° C.; methanol distills off for a period of 2 hours. The precipitate formed after the mixture has been cooled to 120° C. and after 1000 ml of 1-molar hydrochloric acid have been added is separated off over a glass suction filter and recrystallized from acetonitrile. This gives 313 g (82%) of the title product, of melting point 130° C.

A3) Preparing 2-benzotriazol-2-yl-6-tert-butyl-4-[2-(4,5-dihydrooxazol-2yl)ethyl]phenol

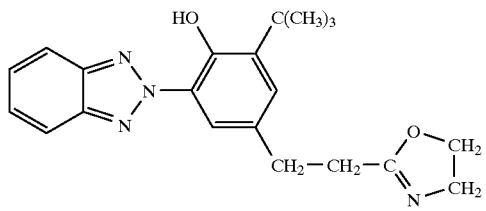

38.3 g (0.1 mol) of the compound described under A2) and 300 ml of ethyl acetate are charged under argon to a 350 ml sulfonating flask with stirrer, condenser and dropping funnel. To the suspension obtained there are added, dropwise at 25° C., 18 g (0.15 mol) of thionyl chloride. The mixture is subsequently stirred at 25° C. for 2 h.

The solid is separated off, washed with ethyl acetate and taken up in 1.5 l of water, and 20 g of sodium bicarbonate are added. After 1 h of stirring, the solid is separated off and recrystallized from methanol. This gives the title product, of melting point 148° C.

The compound of Example A4 is a starting substance for the compound of Example A5.

A4) Preparing 3-(3,5-di-tert-butyl-4-hydroxyphenyl)-N-(2-hydroxyethyl)propionamide (C.A. Reg. No. 40388-53-2)

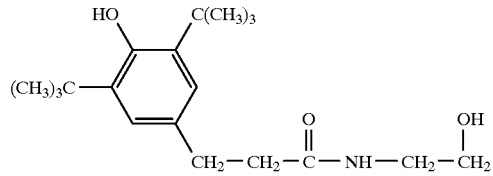

585 g 2.0 mol) of methyl 3-(3,5-di-tert-butyl-4-hydroxyphenyl)-N-(2-hydroxyethyl)propionate [C.A. Reg. No. 6386-38-5] and 244 g (4.0 mol) of ethanolamine are charged to a 2.5 l sulfonating flask with stirrer and distillation attachment.

The mixture is heated to 140° C. under nitrogen, during which methanol distills off. After the reaction has subsided the mixture is cooled to 100° C.; the precipitate formed following the addition of 1 l of 2-molar hydrochloric acid is separated off and recrystallized from 1.5 l of acetonitrile. This gives 500 g of the title product, of melting point 129° C.

A5) Preparing 2,6-di-tert-butyl-4-[2-(4,5-dihydrooxazol-2-yl)ethyl]phenol (C.A. Reg. No. 92176-18-6)

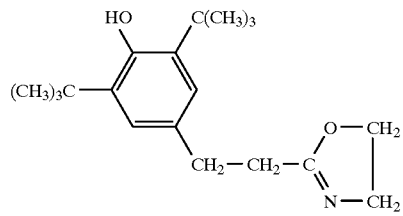

10.0 g (0.03 mol) of the compound prepared under A4) and 20 g of Al$_2$O$_3$ activated at 300° C. under a high vacuum are charged to a ball-tube oven. The mixture is heated slowly under a high vacuum until the product distills off. The distillate is recrystallized from acetonitrile. This gives the title product, of melting point 127° C.

B) Preparing Modified Organic Material B1) 20 g of a copolymer of ethylene and acrylic acid with an acrylic acid content of 9.5% by weight, corresponding to 28 mmol of COOH (manufacturer: DOW) and 5.8 g of the product from Example A5) are reacted in a Brabender PlastiCorder® type PL 2000-6 at 220° C. under argon at a speed of rotation of 60/min for 15 minutes.

Elemental analysis: 0.98% N (calculated: 1.04% N).

To determine the degree of fixation, the material obtained is subjected to the following tests:

A sample of the modified polymer is dissolved in 1,2-dichlorobenzene and the solution is analysed by GC. The residual content of free oxazoline compound is 1% of the amount originally added.

5 g portions of the pulverized product are each extracted for 24 h with hot methylene chloride and with hot methanol; they are then dried and the nitrogen content is determined again. Result: 0.95% N after extraction with methylene chloride; 0.97% N after extraction with methanol.

The tests demonstrate that the stabilizer employed has been bound almost quantitatively to the polymer.

B2) 20 g of a copolymer of ethylene and acrylic acid with an acrylic acid content of 9.5% by weight, corresponding to 28 mmol of COOH (manufacturer: DOW) and 7.0 g of the product from Example A3) are reacted in a Brabender PlastiCorder® type PL 2000-6 at 220° C. under argon at a speed of rotation of 60/min for 15 minutes.

Elemental analysis: 3.99% N (calculated: 3.99% N).

A sample of the modified polymer is dissolved in 1,2-dichlorobenzene and the solution is analysed by GC. The residual content of free oxazoline compound is 1% of the amount originally added.

The stabilizer employed is bound almost quantitatively to the polymer.

C) Stabilizing Organic Material

Example C1: Light stabilization of polypropylene fibres 2.5 g portions of the novel stabilizer from above Examples A3 and A5 respectively together with 1 g of tris(2,4-di-tert-butylphenyl)phosphite, 1 g of calcium monoethyl 3,5-di-tert-butyl-4-hydroxybenzylphosphonate, 1 g of calcium stearate and 2.5 g of $TiO_2$ (Kronos RN 57) are mixed with 1000 g of polypropylene powder (Moplen® FLF20) in a turbomixer (melt index 12 g/10 min, measured at 230° C./2.16 kg).

The mixtures are extruded to granules at 230° C.; these granules are subsequently processed under the following conditions with the aid of a pilot plant (Leonard; Sumirago/VA., Italy) to form fibres:

Extruder temperature: 230–240–245–260–255–255° C.

Draw ratio: 1:3.5

Drawing temperature: 100° C.

Fibres: 12 den

The fibres thus produced are exposed against a white background in a Weather-O-Meter® type 65WR (Atlas Corp.) with a black standard temperature of 63° C. in accordance with ASTM D 2565-85. After different exposure times, the remaining tensile strength of the samples is measured. The measurements are used to calculate the exposure time $T_{50}$ after which only 50% of the original tensile strength is still present.

For comparison purposes, fibres without novel stabilizer are produced and tested under otherwise identical conditions. The fibres stabilized in accordance with the invention show outstanding retention of strength.

Example C2: Light stabilization of polypropylene tapes 1.0 g portions of the novel stabilizer from above Examples A3 and A5 respectively together with 0.75 g of tris(2,4-di-tert-butylphenyl)phosphite, 0.75 g of calcium monoethyl 3,5-di-tert-butyl-4-hydroxybenzylphosphonate and 1 g of calcium stearate are mixed with 1000 g of polypropylene powder in a turbomixer (melt index 4.0 g/10 min, measured at 230° C./2.16 kg). The mixtures are extruded to granules at 200–230° C.; these granules are subsequently processed under the following conditions with the aid of a pilot plant (Leonard; Sumirago/VA., Italy) to form drawn tapes 50 μm thick and 2.5 mm wide:

Extruder temperature: 210–230° C.

Head temperature: 240–260° C.

Draw ratio: 1:6

The tapes thus produced are exposed against a white background in a Weather-O-Meter® type 65WR (Atlas Corp.) with a black standard temperature of 63° C. in accordance with ASTM D 2565-85. After different exposure times, the remaining tensile strength of the samples is measured. The measurements are used to calculate the exposure time T50 after which only 50% of the original tensile strength is still present.

For comparison purposes, tapes without novel stabilizer are produced and tested under otherwise identical conditions.

The tapes stabilized in accordance with the invention show outstanding retention of strength.

Example C3: Stabilization of a 2-coat metallic finish

The compound to be tested is incorporated into 5–10 g of xylene and tested in a clearcoat having the following composition:

| | |
|---|---:|
| Synthacryl ® SC 303[1) | 27.51 |
| Synthacryl ® SC 370[2) | 23.34 |
| Maprenal ® MF 650[3) | 27.29 |
| Butyl acetate/butanol (37/8) | 4.33 |
| Isobutanol | 4.87 |
| Solvesso ® 150[4) | 2.72 |
| Kristallöl K-30[5) | 8.74 |
| Levelling assistant Baysilon ® MA[6) | 1.20 |
| | 100.00g |

[1)Acrylate resin from Hoechst AG; 65% solution in xylene/butanol 26:9
[2)Acrylate resin from Hoechst AG; 75% solution in Solvesso ® 100[4)
[3)Melamine resin from Hoechst AG; 55% solution in isobutanol
[4)aromat. hydrocarbon mixture, boiling range 182–203° C. (Solvesso ® 150) or 161–178° C. (Solvesso ® 100); manufacturer: ESSO
[5)aliphat. hydrocarbon mixture, boiling range 145–200° C.; manufacturer: Shell
[6)1% in Solvesso ® 150[4); manufacturer: Bayer AG 1.275% of the compound from Example A3 to be tested are added to the clearcoat, based on the solids content of the coating material. A number of further coating-material samples are prepared which in addition to the novel compound contain 1% of the compound

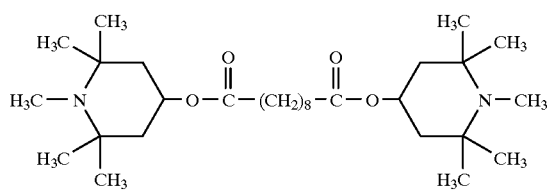

(compound A) based on the solids content of the coating material. A clearcoat containing no light stabilizer is used as comparison.

The clearcoat is diluted to spray viscosity with Solvesso® 100 and is sprayed onto a prepared aluminium panel (coil coat, filler, light green metallic basecoat) and stoved at 130° C. for 30 minutes. The result is a clearcoat film with a dry thickness of 40–50 μm.

The samples are then weathered in a UVCON® weathering apparatus from Atlas Corp. (UVB-313 lamps) with a cycle of 8 h of UV irradiation at 70° C. and 4 h condensation at 50° C.

The surface gloss (20° gloss in accordance with DIN 67530) of the samples is measured at regular intervals.

The samples stabilized in accordance with the invention have better weathering stability (gloss retention, crack resistance) than the unstabilized comparison sample.

Example C4: A copolymer of ethylene and acrylic acid with an acrylic acid content of 9.5% by weight (Primacor®

3440; manufacturer: DOW) is modified as described in example B2) except that only 5% by weight (based on the weight of the polymer) of the product from Example A3) are added and the reaction is carried out using a twin screw extruder (Haake type TW 100) at maximum temperature 240° C.

The stabilizer employed is bound almost quantitatively to the polymer.

The modified polymer is compounded with a mixture of 70% by weight of LDPE (Lupolen® 3026 F from BASF) and 30% by weight of polyamide 6 (Ultramid® B36, predried, from BASF) in a twin screw extruder (Haake type TW 100) at 240° C. and a rotational speed of 75 per minute and formed to test pieces for measuring tensile impact strength according to ISO DIS 3167.

The amount of modified polymer added is 4% and 8% by weight of the sum of LDPE and polyamide 6. For comparison purposes, some samples are prepared using unmodified copolymer of ethylene and acrylic acid.

The samples are stored in naphta at 20–25° C. for a period of 25 days. After drying, they are exposed against a white background in a Weather-O-Meter® type 65WR (Atlas Corp.) with a black standard temperature of 63° C. and a relative humidity of 60%. At regular intervals, the yellowness index (YI, ASTM D 1925) and the tensile impact strength (DIN 53448) are determined.

The samples stabilized according to the invention show no discoloration and an excellent stability against weathering.

What is claimed is:

1. A compound of the formula I

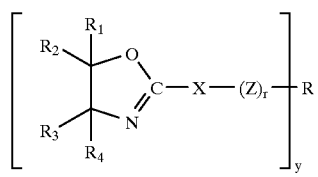

(I)

where r is 0 or 1 and y is a number from the range 1–3;

X is a direct bond or —$NR_8$—, —CO—, —CONH— or —COO— or a divalent aliphatic or mixed aromatic-aliphatic $C_1$–$C_{18}$hydrocarbon radical;

Z is an aromatic, aliphatic or mixed aromatic-aliphatic $C_3$–$C_{18}$ hydrocarbon radical which is interrupted in the aliphatic moiety by a divalent functional group in a carbon-carbon single bond, and/or interrupted in the aromatic or aliphatic moiety by a divalent functional group in a carbon-hydrogen bond, the functional group being selected from the group consisting of —O—, —$NR_8$—, —S—, —SO—, —$SO_2$—, —CONH—, —CO— and —COO—;

R is a mono-, di- or trivalent radical of a sterically hindered amine stabilizer or of a UV absorber selected from 2-hydroxyphenylbenzotriazoles, 2-hydroxyphenylbenzophenones, oxalanilides or 2-hydroxyphenyl-4,6-diaryltriazines or a di- or trivalent radical of a sterically hindered phenol;

$R_1$ and $R_2$, independently of one another, are H or $C_1$–$C_{12}$alkyl;

$R_3$ and $R_4$, independently of one another, are H, $C_1$–$C_{18}$alkyl or —X—(Z)$_r$—$R_5$;

$R_5$ is a monovalent radical of a sterically hindered amine stabilizer or of a UV absorber selected from 2-hydroxyphenylbenzotriazoles, 2-hydroxyphenylbenzophenones, oxalanilides or 2-hydroxyphenyl-4,6-diaryltriazines or a radical of a sterically hindered phenol; and $R_8$ is H, $C_1$–$C_{18}$alkyl, $C_7$–$C_{11}$phenylalkyl, $C_2$–$C_6$alkoxyalkyl or $C_5$–$C_{12}$cycloalkyl.

2. A compound according to claim 1 of the formula I, in which

R, if y is 1, is a monovalent radical $Z_1$—$R_5$,

R, if y is 2, is a divalent radical $Z_2$—$R_6$, and

R, if y is 3, is a trivalent radical $Z_3$—$R_7$; and $Z_1$ comprises the meanings given for X—(Z)$_r$;

$Z_2$ is a divalent radical having the meaning indicated for $Z_1$ or is a trivalent aliphatic or mixed aromatic-aliphatic $C_1$–$C_{18}$ hydrocarbon radical, which is interrupted in the aliphatic moiety by a divalent functional group in a carbon-carbon single bond and/or is substituted by OH and/or is attached via a divalent or trivalent functional group, or is

the functional group being selected from the group consisting of —O—, —$NR_8$—, —S—, —SO—, —$SO_2$—, —CO—, —CONH—, —COO— and

$Z_3$ is divalent, trivalent or tetravalent and comprises the meanings indicated for $Z_2$ or is a tetravalent aliphatic or mixed aliphatic-aromatic $C_1$–$C_{18}$ hydrocarbon radical which is interrupted in the aliphatic moiety by a divalent functional group in a carbon-carbon single bond and/or is substituted by OH and/or is attached via a divalent functional group, the functional group being selected from the group consisting of —O—, —$NR_8$—, —S—, —SO—, —$SO_2$—, —CO—, —CONH— and —COO—;

$R_5$ has one of the formulae

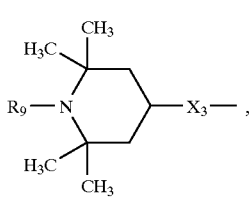

(IIa)

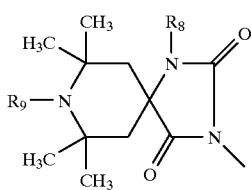

(IIb)

-continued
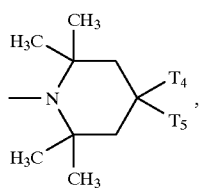   (IIc)
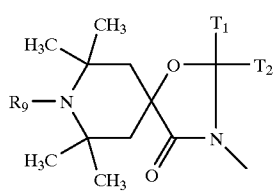   (IId)
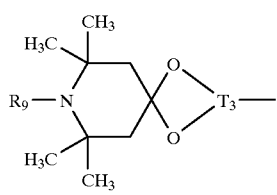   (IIe)
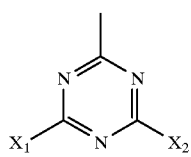   (IIf)
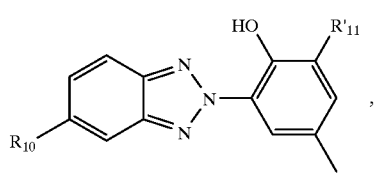   (IIIa)
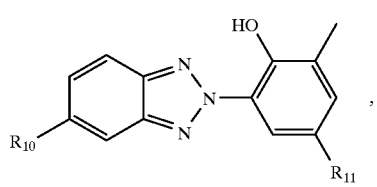   (IIIb)
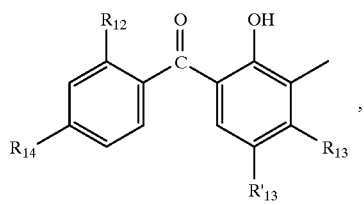   (IVa)
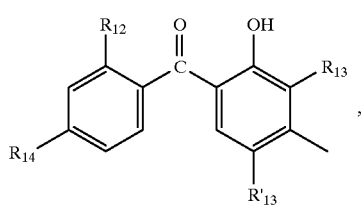   (IVb)
-continued
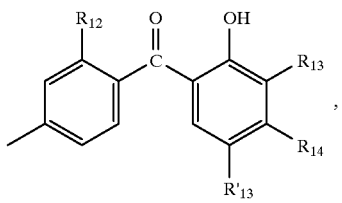   (IVc)
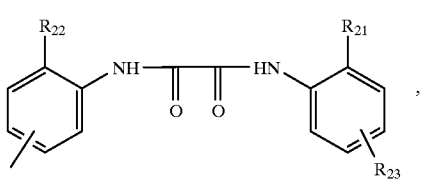   (Va)
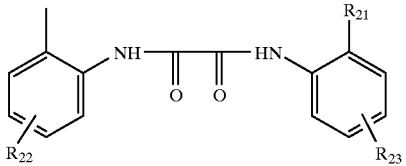   (Vb)
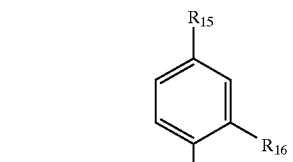   (VIa)
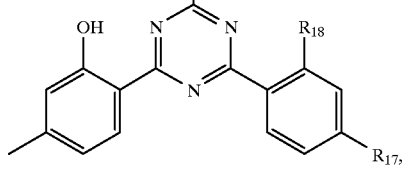   (VIb)
$R_6$ has one of the meanings indicated for $R_5$ or has one of the formulae
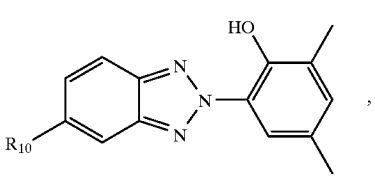   (IIIc)

-continued

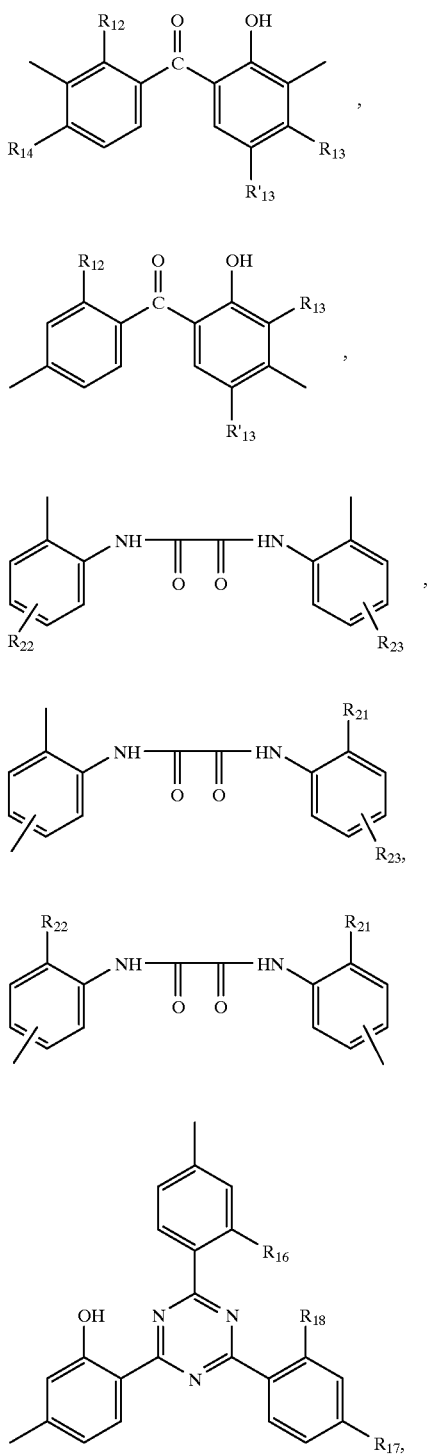

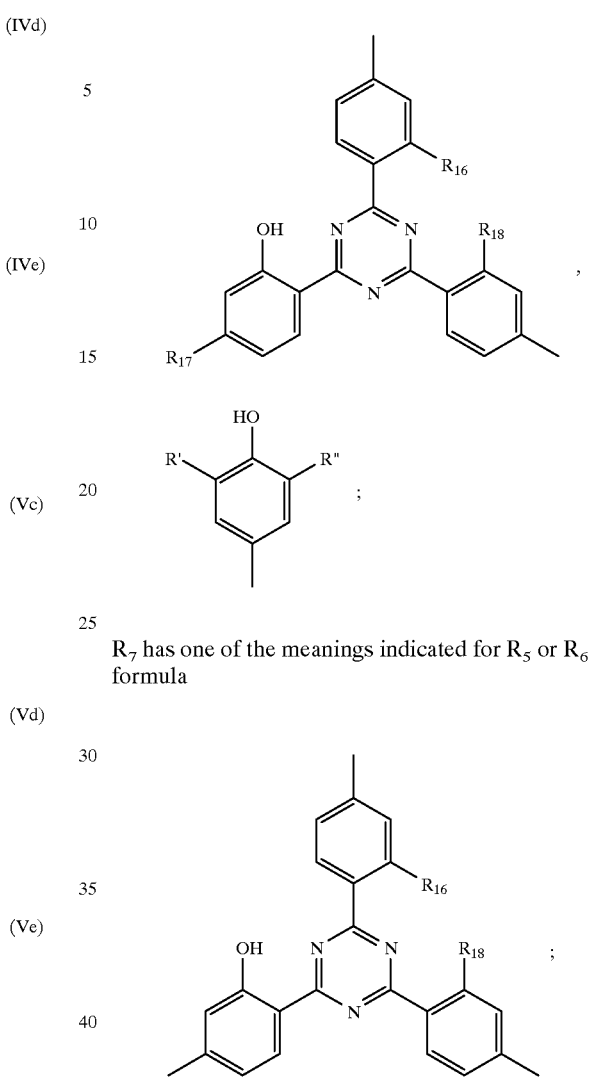

R₇ has one of the meanings indicated for R₅ or R₆ or has the formula in which
R' is $C_1$–$C_{18}$alkyl or cyclohexyl, and
R" is tert-$C_4$–$C_{18}$alkyl or cyclohexyl;
$R_8$ is H, $C_1$–$C_{18}$alkyl, $C_7$–$C_{11}$phenylalkyl, $C_2$–$C_6$alkoxyalkyl or $C_5$–$C_{12}$cycloalkyl;
$R_9$ is hydrogen, oxyl, hydroxyl, $C_1$–$C_{18}$alkyl, $C_3$–$C_8$alkenyl, $C_3$–$C_8$alkynyl, $C_7$–$C_{12}$aralkyl, $C_1$–$C_{18}$alkoxy, $C_5$–$C_{12}$cycloalkoxy, $C_7$–$C_9$phenylalkoxy, $C_1$–$C_8$alkanoyl, $C_3$–$C_5$alkenoyl, $C_1$–$C_{18}$alkanoyloxy, benzyloxy, glycidyl or a group —CH₂CH(OH)—G,
in which G is hydrogen, methyl or phenyl;
$R_{10}$ is H, Cl, $C_1$–$C_4$alkyl or $C_1$–$C_4$alkoxy;
$R_{11}$ is $C_1$–$C_{12}$alkyl;

$R'_{11}$ is H or $C_1$–$C_{12}$alkyl;

$R_{12}$ is H or OH;

$R_{13}$ is H, Cl, OH or $C_1$–$C_{18}$alkoxy;

$R'_{13}$ is H, Cl or $C_1$–$C_4$alkyl;

$R_{14}$ is H, Cl, OH or $C_1$–$C_{18}$alkoxy;

$R_{15}$ and $R_{17}$, independently of one another, are H, OH, Cl, CN, phenyl, $C_1$–$C_6$alkyl, $C_1$–$C_{18}$alkoxy, $C_4$–$C_{22}$alkoxy which is interrupted by O and/or substituted by OH, or are $C_7$–$C_{14}$phenylalkoxy; and $R_{16}$ and $R_{18}$, independently of one another, are H, OH, Cl, $C_1$–$C_6$alkyl or $C_1$–$C_6$alkoxy;

$R_{19}$ and $R'_{19}$, independently of one another, have one of the meanings indicated for $R_8$ or together form tetramethylene or -oxamethylene or pentamethylene or -oxamethylene;

$R_{20}$ is $C_1$–$C_{18}$alkyl, $C_2$–$C_4$alkenyl or phenyl;

$R_{21}$, $R_{22}$ and $R_{23}$, independently of one another, are H, $C_1$–$C_{18}$alkyl or $C_1$–$C_{18}$alkoxy;

$T_1$ and $T_2$, independently of one another, are hydrogen, $C_1$–$C_{18}$alkyl, phenyl-$C_1$–$C_4$alkyl or unsubstituted or halogen- or $C_1$–$C_4$alkyl-substituted phenyl or naphthyl or $T_1$ and $T_2$, together with the carbon atom connecting them, form a $C_5$–$C_{12}$cycloalkane ring, $T_3$ is $C_2$–$C_8$alkanetriyl;

$T_4$ is hydrogen, $C_1$–$C_{18}$alkoxy, $C_3$–$C_8$alkenyloxy or benzyloxy, and $T_5$ has the same meaning as $T_4$, or $T_4$ and $T_5$ together are —O-$C_2$–$C_8$alkylene-O—, or $T_5$, if $T_4$ is hydrogen, is —OH or —NR$_8$—CO—R$_{20}$;

$X_1$ is a group of the formula IIa and $X_2$ has the same meaning as $X_1$ or is $C_1$–$C_{18}$alkoxy or —NR$_{19}$R'$_{19}$;

$X_3$ is —NR$_8$—, —NX$_6$— or —O—, or is a radical of the formula —O—CO—X$_5$—CO—O—X$_6$, where $X_5$ is $C_1$–$C_{12}$alkanetriyl and $X_6$ is a radical of the formula

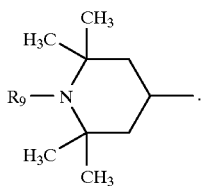

3. A compound according to claim 2 of one of the formulae Ia–Ie,

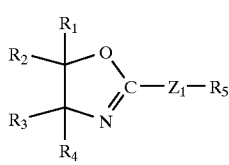  (Ia)

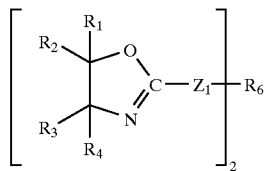  (Ib)

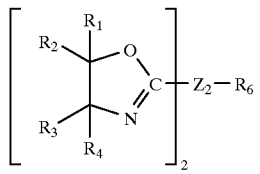  (Ic)

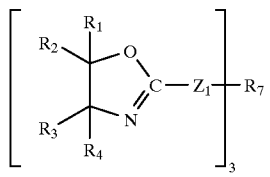  (Id)

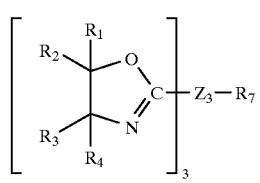  (Ie)

in which $R_1$ and $R_2$, independently of one another, are H or $C_1$–$C_{12}$alkyl;

$R_3$ and $R_4$, independently of one another, are H, $C_1$–$C_{18}$alkyl or —Z$_1$—R$_5$;

$Z_1$ is phenylene, a divalent selected from one of the formulae -phenylene-$Z_4$—, -phenylene-$Z_5$—, —$Z_4$—$Z_5$ or X—$Z_4$—$Z_5$, where $Z_5$ does not bond to the oxazoline ring; or $Z_1$ has one of the meanings indicated for $Z_4$ or X;

$Z_2$ is a trivalent radical T, T—$Z_5$, T—($Z_5$)$_2$, X—T, (X)$_2$—T, X—T—$Z_5$, (X)$_2$—T—$Z_5$ or X—T—($Z_5$)$_2$, where X bonds to the oxazoline ring and $Z_5$ bonds to $R_6$ and T is $C_1$–$C_{12}$alkanetriyl or $C_3$–$C_{12}$alkanetriyl which is interrupted by phenylene, cyclohexylene and/or is substituted by OH;

$Z_3$ is a tetravalent radical D, D—$Z_5$, D—($Z_5$)$_2$, D—($Z_5$)$_3$, X—D, (X)$_2$—D, (X)$_3$—D, X—D—$Z_5$, (X)$_2$—D—$Z_5$, (X)$_3$—D—$Z_5$, X—D—($Z_5$)$_2$ or X—D—($Z_5$)$_3$, where X bonds to the oxazoline ring and $Z_5$ bonds to $R_7$ and D is $C_1$–$C_{12}$alkanetetrayl or is $C_3$–$C_{12}$alkanetetrayl which is interrupted by phenylene, cyclohexylene and/or is substituted by OH;

$Z_4$ is $C_1$–$C_{12}$alkylene or is $C_2$–$C_{12}$alkylene which is interrupted by phenylene, cyclohexylene, and/or is substituted by OH; and $Z_5$ is —O—, —NR$_8$—, —S—, —SO—, —SO$_2$—, —CO—, —CONR$_8$— or —COO—.

4. A compound according to claim 1 of one of the formulae Ia–Id

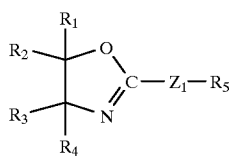  (Ia)
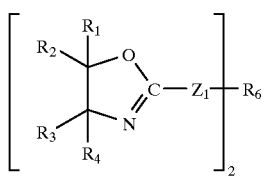  (Ib)
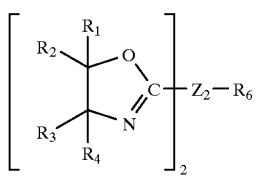  (Ic)
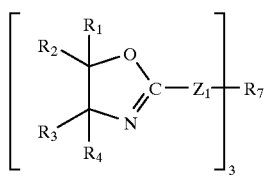  (Id)
in which
R$_3$ and R$_4$, independently of one another, are H or C$_1$–C$_{12}$alkyl;
R$_5$ has one of the formulae
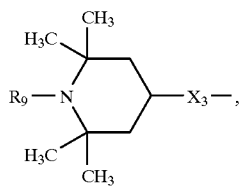  (IIa)
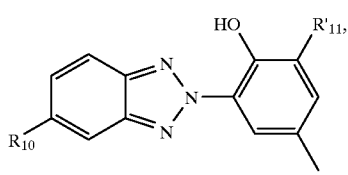  (IIIa)
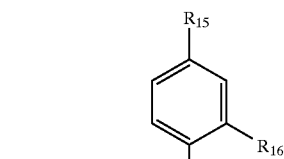  (VIa)
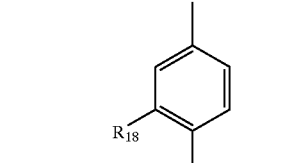  (VIb)
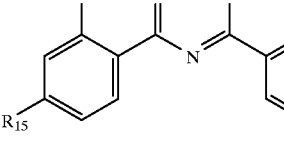  (VIc)
R$_6$ has one of the meanings indicated for R$_5$ or has one of the formulae
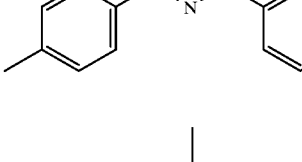  (VId)

-continued

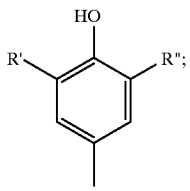
(VIIa)

and
$R_7$ has the formula

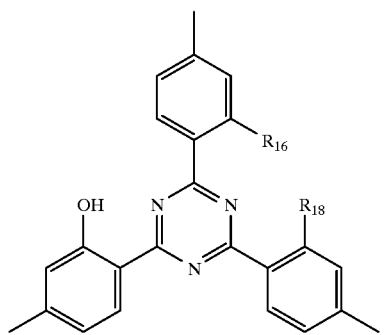
(VIe)

in which
R' is methyl, tert-butyl or cyclohexyl and
R" is tert-butyl or cyclohexyl;
$R_8$ is H, $C_3$–$C_8$alkyl, benzyl or cyclohexyl;
$R_9$ is hydrogen, methyl, $C_6$–$C_{12}$alkoxy or cyclohexyloxy;
$R_{10}$ is H, Cl, methyl or methoxy;
$R_{15}$ and $R_{17}$, independently of one another, are H, OH, Cl, phenyl, methyl, $C_1$–$C_{18}$alkoxy, $C_4$–$C_{22}$alkoxy which is interrupted by O and/or substituted by OH, or are benzyloxy; and
$R_{16}$ and $R_{18}$, independently of one another, are H, OH, Cl, or methyl; and $X_3$ is —$NR_8$— or —O—;
$Z_1$ is a divalent group of one of the formulae —$Z_4$—$Z_5$ or X—$Z_4$—$Z_5$, where $Z_5$ does not bond to the oxazoline ring; or $Z_1$ has one of the meanings indicated for $Z_4$ or X;
$Z_2$ is a trivalent radical T, T—$Z_5$, T—$(Z_5)_2$, where $Z_5$ bonds to $R_6$ and T is $C_1$–$C_{12}$alkanetriyl or OH-substituted $C_3$–$C_{12}$alkanetriyl;
$Z_3$ is a tetravalent radical D, D—$Z_5$, D—$(Z_5)_2$ or D—$(Z_5)_3$, where $Z_5$ bonds to $R_7$ and
D is $C_1$–$C_{12}$alkanetetrayl or OH-substituted $C_3$–$C_{12}$alkanetetrayl;
$Z_4$ is $C_1$–$C_{12}$alkylene or is $C_3$–$C_{12}$alkylene which is interrupted by phenylene and/or
$Z_5$ and/or is substituted by OH; and
$Z_5$ is —O—, —$NR_8$— or —COO—.

5. A composition comprising as component A an organic material which is sensitive to oxidative, thermal and/or actinic degradation, and as component B a compound of the formula I according to claim 1.

6. A composition according to claim 5 comprising as component A a thermoplastic polymer or a film-forming binder for coatings.

7. A composition according to claim 5 comprising from 0.01 to 10% by weight of the compound of component B, based on the material to be stabilized.

8. A composition according to claim 5 comprising as additional component C a further additive.

9. A method of stabilizing organic material against thermal, oxidative or/and actinic degradation, which comprises adding to this material a compound of the formula I according to claim 1.

10. A method according to claim 9, wherein the organic material is a thermoplastic polymer and which method comprises admixing the compound of the formula I and heating the resulting mixture.

* * * * *